United States Patent [19]

Grego

[11] Patent Number: 4,830,512

[45] Date of Patent: May 16, 1989

[54] METHOD OF MEASURING VISCOSITY OF A BODY

[75] Inventor: Giorgio Grego, Venaria Reale, Italy

[73] Assignee: Cselt-Centro Studi e Laboratori Telecomunicazioni S.p.A., Turin, Italy

[21] Appl. No.: 122,074

[22] Filed: Nov. 18, 1987

[30] Foreign Application Priority Data

Dec. 10, 1986 [IT] Italy ............................. 67920 A/86

[51] Int. Cl.⁴ ...................... G01N 11/02; G01N 25/02
[52] U.S. Cl. ..................................................... 374/54
[58] Field of Search ................ 374/160, 161, 54, 131, 374/123; 356/301, 44, 73.1

[56] References Cited

U.S. PATENT DOCUMENTS

| | | | |
|---|---|---|---|
| 3,424,533 | 1/1969 | Hughes et al. | 356/302 X |
| 3,559,464 | 2/1971 | Foust et al. | 73/55 |
| 3,604,247 | 9/1971 | Gramain | 73/55 |
| 4,105,337 | 8/1978 | Bjorklund et al. | 374/130 X |
| 4,299,393 | 11/1981 | Benckert et al. | 350/96.24 X |
| 4,396,290 | 8/1983 | Morris | 356/350 |
| 4,403,502 | 9/1983 | Lindt | 73/55 |
| 4,516,864 | 5/1985 | Kim et al. | 374/131 X |
| 4,724,316 | 2/1988 | Morton | 350/96.29 |
| 4,767,219 | 8/1988 | Bibby | 374/123 |

OTHER PUBLICATIONS

"Laser Techniques (Thermal, Optical)", Ultrasonci Testing, by L. Szilard, TA 417.4 4.4, 1982 (pp. 190-191, 402-407) 374-117 (Sep. 65).
GB 2140 554 UK Patent Application, 11/28/84, (1984), D. P. Dakin, 5 pages.

Primary Examiner—Daniel M. Yasich
Attorney, Agent, or Firm—Herbert Dubno

[57] ABSTRACT

The method of measuring viscosity of a glass body, such as an optical preform related to at least its softening temperature, exploits the scattering effects the body introduces into a substantially monochromatic radiation passing through it; more particularly, the width of the spectral line due to Brillouin scattering is measured. The temperature of the body can also be determined by measuring the width of the line generated by Rayleigh scattering. The method is of particular interest for measurements on glasses.

10 Claims, 1 Drawing Sheet

METHOD OF MEASURING VISCOSITY OF A BODY

FIELD OF THE INVENTION

The present invention relates to a method of measuring viscosity of a body. Preferably, but not exclusively, the method is employed for on-line monitoring of the characteristics of an optical fiber preform.

BACKGROUND OF THE INVENTION

It is known that in many manufacturing processes requiring heating of materials being treated, an on-line, point-by-point monitoring of material viscosity would be desirable, as deviations from a desired viscosity profile could alter the characteristics of the final material. In particular, in drawing optical fibers preforms which comprise layers with non-uniform composition (for instance because of different dopant concentrations), it is important to monitor viscosity throughout the entire preform cross-section, in the softening region of the preform.

The literature does not disclose techniques for on-line direct monitoring of viscosity of a body, in particular a body which is in fluid condition or whose behavior can be treated as that of a fluid (e.g. a glass). Viscosity information could be contained for instance from temperature values, measured by means of pyrometers. Yet temperature information supplied by a pyrometer cannot be used to obtain viscosity when the latter is to be determined near the softening temperature. In effect, considering for instance a vitreous body, like an optical fiber preform, viscosity variations of the order of $10^6$ occur within an interval of few degrees centigrade. The precise determination of viscosity would require measurement of temperature variations of the order of 1° C. in a body which is for instance at a temperature of about 2000° C., and industrial pyrometers do not have such sensitivity.

OBJECT OF THE INVENTION

The object of the invention is to provide a method allowing direct measurement of the viscosity of a body, with a very high measurement precision.

SUMMARY OF THE INVENTION

The invention is based upon the phenomenon that, when an electromagnetic radiation (e.g. a light beam) is sent into a body such as a glass (i.e. a fluid body), the scattered radiation exhibits frequency alterations depending inter alia on body viscosity.

Among the various scattering phenomena, Brillouin scattering is of particular interest for the present invention: this scattering gives rise to two spectral lines, at both sides of the spectral line of the incident radiation, with a line width:

$$\delta\nu_B = \frac{4\eta k^2}{2\pi\rho_o} \sin^2 \theta/2 \quad (1)$$

where:
- $\eta$ = viscosity of the body;
- $k = 2\pi n/\lambda$ = wave vector of the incident radiation (n = refractive index of the body, $\lambda$ = wavelength of the radiation)
- $\rho_o$ = density of the body
- $\theta$ = angle of observation.

The viscosity is therefore given by $$\eta = \frac{2\pi\rho_o}{4k^2 \cdot \sin^2 \frac{\theta}{2} \cdot \delta\nu_B}$$

where $\delta\nu_B$ is measured and all other quantities on the right side of the equation are characteristics of the material examined or are selected by the observer ($\theta$).

Therefore, according to the present invention, at least a first beam of a substantially monochromatic light radiation is sent into the body under test, the beam scattered by the body is collected according to a predetermined observation angle; the width of at least one line generated in the radiation spectrum due to Brillouin scattering is measured; and the viscosity of the body region traversed by the beam is obtained from the measured linewidth.

Obviously, the described operations provide information only on the viscosity of the body portion traversed by the measurement beam. This is sufficient if the body is substantially homogeneous.

In case of a non-homogeneous body, the viscosity of a first, substantially homogeneous portion could be first determined, and then the measure will be repeated, by varying the beam position, so that the beam passes through a different, substantially homogeneous body portion at each subsequent measurement. The information about each new portion will be obtained by difference with respect to the preceding measurement.

For instance, in case of measurements on an optical fiber preform comprising a plurality of coaxial layers, a first measurement will be carried out on the outer preform layer and then the beam will be displaced step by step parallel to itself so as to pass through a different layer at each subsequent step.

Information could also be simultaneously obtained in a plurality of sections taken in different planes, in particular in two perpendicular planes. To this end two or more beams are to be used, each beam being displaceable parallel to itself in one said plane. For instance, in the case of optical fiber preforms, a measurement in axial direction and a measurement on an entire section perpendicular to the preform axis can be effected.

Preferably, the measurements are carried out on the backscattered beam (observation angle $\theta = 180°$) as this makes value $\delta\nu_B$ a maximum, as clearly shown by relation (1), thereby facilitating the measurement.

A method as described has a very high measurement precision. In fact, line as known, width $\delta\nu_B$ is of the order of 10 MHz and the commercially available apparatus for spectrometric measurements allow such a value to be measured with a precision that, depending on the greater or lesser apparatus sophistication, ranges from about 1 KHz to 1 Hz or a fraction of a Hz. Thus, viscosity variations ranging from $10^{-4}$ to $10^{-7}$, or even smaller, can be appreciated.

It is also to be appreciated that the scattered radiation spectrum, besides the lines due to Brillouin scattering, has a further line, centered on the incident radiation frequency and having a width:

$$\delta\nu_{RW} = \frac{3kt_o}{8\pi^2 a^3 \eta} \quad (3)$$

where k, $\eta$ have the same meaning as in relation (1), and To and a are the temperature in °K. and the radius of the particles forming the body, respectively. This can by transposition, yield the relation:

$$T_o = \delta\nu_{RW} \cdot 8\pi^2 a^3 \eta / 3k \quad (4)$$

Thus, according to the invention, besides $\delta\nu_B$, also $\delta\nu_{RW}$ could be measured to determine also the body temperature. A further control parameter for the monitored process is thus available.

The method disclosed can be carried out using conventional apparatus for Brillouin spectrometry.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
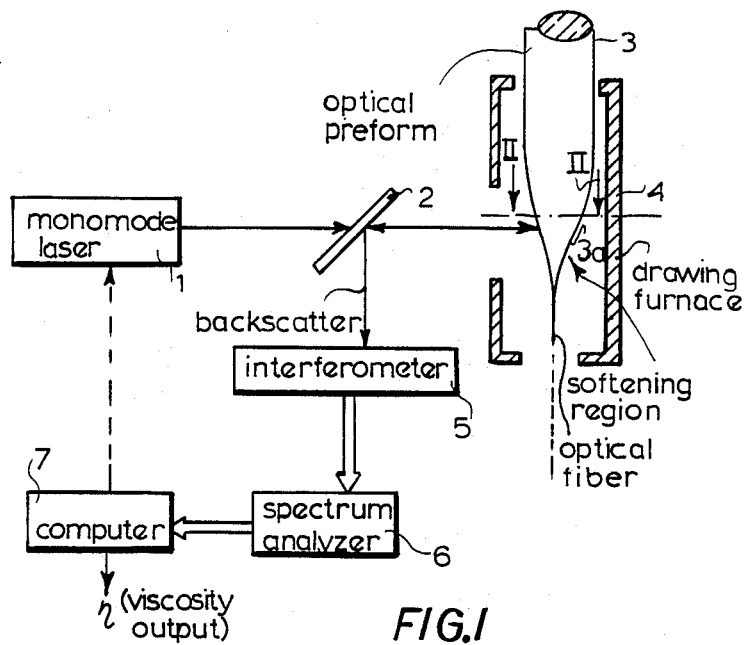
FIG. 1 is a block diagram illustrating the method of the invention.

In the drawing, the beam outgoing from a source 1, e.g. a monomode laser, is sent through a beam splitter 2 onto an optical fiber preform 3 located in a drawing furnace 4 (i.e. a body which in at least the fiber-drawing region is flowable). The beam is so oriented as to impinge for instance at the softening region 3a. The backscattered beam is reflected by beam splitter 2 towards a Fabry-Perot interferometer 5, whose output signal is fed to a spectrum analyzer 6 sending the values of $\delta\nu_B$ to a computer 7 which computes the value of $\eta$ according to relation (1).

Figure 2:
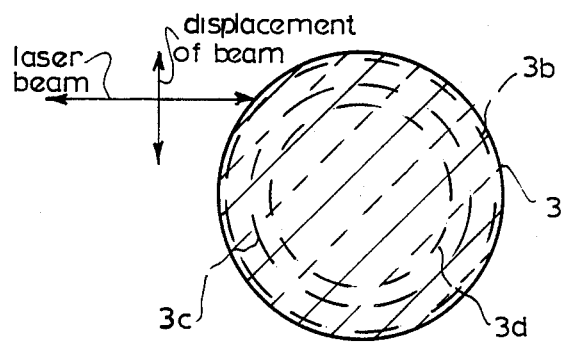
FIG. 2 is a cross sectional view along lines II—II of FIG. 1.

Source 1 is mounted on a support (not shown) allowing the source to be displaced parallel to itself to obtain the viscosity over a whole plane cross-section of preform 3, i.e. through the successive layers 3b, 3c, 3d. (FIG. 2)

A second apparatus like that described above could be arranged to send a light beam parallel to the axis of preform 3, so as to supply viscosity information relevent to the axial direction.

A second measure by the same apparatus may provide the width $\delta\nu_{RW}$ of the Rayleigh scattering line; by supplying computer 7 with such a value, also the body temperature can be obtained.

I claim:

1. A method of measuring viscosity of a flowable body, comprising the steps of:
   introducing a first beam of substantially monochromatic light into the flowable body at a body region thereof constituted of a material of the body capable of transmitting light;
   collecting a second beam scattered by the body at a predetermined observation angle;
   measuring a line width $\delta\nu_B$ of at least one line generated in a radiation spectrum of the second beam and due to Brillouin scattering; and
   calculating the viscosity $\eta$ of the body region traversed by the first beam from the measured linewidth $\delta\nu_B$ in accordance with the relationship:

$$\eta = \frac{2\pi\rho_o}{4k^2 \cdot \sin^2\frac{\theta}{2} \cdot \delta\nu_B}$$

where k and $\rho_o$ are constants characteristic of a material of said body and $\theta$ is said observation angle.

2. The method defined in claim 1, wherein said angle is 180°.

3. The method defined in claim 1 wherein said body is a non-homogeneous body having a plurality of substantially homogenous body regions, said first beam is sent into a first of said, substantially homogeneous body regions and the viscosity of said first region is calculated; and the measurements are repeated, by varying the first beam position so that the first beam passes through a different, substantially homogeneous body regions at each subsequent measurement and the viscosity of each new region is obtained in terms of a difference with respect to a preceding measurement.

4. The method defined in claim 1 wherein said body is an optical fiber preform comprising a plurality of coaxial layers, and the measurement is carried out by displacing the first beam parallel to itself so as to obtain a viscosity measurement over an entire area of a plane preform section.

5. The method defined in claim 4 wherein the viscosity of said preform while it undergoes a thermal treatment required for the drawing of an optical fiber is measured, and said plane section is a section taken in a softening region of the preform constituting said flowable body.

6. The method defined in claim 4 wherein said plane section is perpendicular to an axis of the preform.

7. The method defined in claim 6 wherein the second beam is sent into said optical fiber preform in a direction parallel to the preform axis.

8. The method defined in claim 1 wherein the viscosity is determined over an entire plane section comprising said second direction by changing the second beam position.

9. The method defined in claim 1 wherein at least a second monochromatic beam is sent into the body along a second direction different from the direction of said first beam, and the viscosity of the body at least in said second direction is also measured.

10. The method defined in claim 1, further comprising the step of measuring a line width $\delta\nu_{RW}$ of a line due to Rayleigh scattering in the scattered second beam, to determine the temperature in the region traversed by the second beam in accordance with the relationship:

$$T_o = \delta\nu_{RW} \cdot 8\pi^2 a^3 \eta / 3k \quad (4)$$

where a is a constant of the material.

* * * * *